(12) United States Patent
Mölter et al.

(10) Patent No.: US 7,139,075 B2
(45) Date of Patent: Nov. 21, 2006

(54) METHOD AND APPARATUS FOR MEASURING THE SIZE DISTRIBUTION AND CONCENTRATION OF PARTICLES IN A FLUID

(75) Inventors: Leander Mölter, Wörth (DE); Friedrich Munzinger, Gondelsheim (DE)

(73) Assignee: Palas GmbH Partikel-und Lasermestechnik, Karlsruhe (DE)

( * ) Notice: Subject to any disclaimer, the term of this patent is extended or adjusted under 35 U.S.C. 154(b) by 315 days.

(21) Appl. No.: 10/351,421

(22) Filed: Jan. 27, 2003

(65) Prior Publication Data

US 2003/0142311 A1 Jul. 31, 2003

(30) Foreign Application Priority Data

Jan. 26, 2002 (DE) ................ 102 02 999

(51) Int. Cl.
*G01N 15/02* (2006.01)
*G01N 21/00* (2006.01)

(52) U.S. Cl. ..................... 356/336; 356/337
(58) Field of Classification Search ......... 356/335–343
See application file for complete search history.

(56) References Cited

U.S. PATENT DOCUMENTS

| | | | | |
|---|---|---|---|---|
| 3,797,937 A | * | 3/1974 | Shofner | ............ 356/336 |
| 4,037,965 A | | 7/1977 | Weiss | |
| 4,249,244 A | * | 2/1981 | Shofner et al. | ............ 250/573 |
| 4,281,924 A | | 8/1981 | Auer et al. | |
| 4,422,761 A | * | 12/1983 | Frommer | ............ 356/338 |
| 4,779,003 A | | 10/1988 | Tatsuno | |
| 4,943,159 A | * | 7/1990 | Oetliker et al. | ............ 356/73 |
| 5,194,921 A | | 3/1993 | Tambo et al. | |
| 5,751,422 A | * | 5/1998 | Mitchell | ............ 356/337 |
| 5,815,265 A | | 9/1998 | Mölter et al. | |
| 6,819,411 B1 | * | 11/2004 | Sharpe et al. | ............ 356/72 |

FOREIGN PATENT DOCUMENTS

| | | |
|---|---|---|
| DE | 35 34 973 A1 | 4/1987 |
| DE | 92 04 322 U1 | 9/1992 |
| DE | 196 11 931 A1 | 10/1997 |
| DE | 196 12 569 C1 | 10/1997 |
| DE | 199 10 698 A1 | 9/1999 |
| DE | 200 00 773 U1 | 5/2000 |
| EP | 0 487 189 A2 | 5/1992 |
| EP | 0 791 817 A | 8/1997 |
| WO | WO 86/07455 | 12/1986 |

* cited by examiner

*Primary Examiner*—Hwa (Andrew) Lee
*Assistant Examiner*—Gordon J. Stock, Jr.
(74) *Attorney, Agent, or Firm*—Antonelli, Terry, Stout and Kraus, LLP.

(57) ABSTRACT

A method for measuring the characteristics of particles in a fluid by detecting electromagnetic radiation scattered on individual particles and an apparatus for performing the method are characterized in that the measurement takes place in structurally separated manner using at least one irradiating device and at least one receiver device in at least one sensor arrangement through which flows a fluid flow containing the particles to be measured, that in the at least one sensor arrangement signal formation takes place of a signal to be received in the receiver device using exclusively optomechanical elements and that signals are transmitted between the at least one sensor arrangement and the at least one irradiating device or the at least one receiver device by means of optical signal transmitters. This makes the apparatus particularly suitable for use in explosion-endangered environments and at difficultly accessible measurement locations, e.g. on chimneys.

31 Claims, 6 Drawing Sheets

METHOD AND APPARATUS FOR MEASURING THE SIZE DISTRIBUTION AND CONCENTRATION OF PARTICLES IN A FLUID

FIELD OF THE INVENTION

The invention relates to a method and an apparatus for measuring the characteristics of particles in a fluid by the detection of electromagnetic radiation scattered over individual particles with at least one irradiating device, at least one receiver device and at least one sensor arrangement, through which flows the fluid flow containing the particles to be measured.

BACKGROUND OF THE INVENTION

In the case of a particle flow in a fluid which is to be measured, it can in fact be a question of solid or liquid particles, which are embedded in a gas or in another liquid and moved with the same or which are moved together. Measurements of this type are generally carried out in order to determine the particle size distribution and particle concentration in the fluid and can e.g. be used in space, exhaust air and medical technology. The detection of particles takes place through the stray light intensity scattered by a particle on a receiver, in that the particle flow is irradiated with suitable electromagnetic radiation in the infrared to ultraviolet light range and preferably with white light. Part of the stray radiation is detected by a detector. The particle characteristics which are of interest are determined by means of count pulses, which are evaluated by an evaluation electronics of a suitable nature positioned downstream of the detector.

Such methods and apparatuses are known from DE 196 12 569 C1 and U.S. Pat. No. 5,815,265. For increasing the dynamic range when checking the size distribution of particles in fluids, DE 196 12 569 C1 discloses the provision of two succeeding measuring volumes in a measuring channel through which a fluid flows. The measuring volumes are illuminated by means of a single light source, whose radiation is split by means of an arrangement of at least in part partly reflecting mirrors and lenses into two beam paths. Two photomultipliers are used for detecting the proportional scattered radiation. The illuminating device, the measuring arrangement and the detector arrangement form a constructionally compact unit, which has both optomechanical and electronic components.

In order to avoid particle detection errors in marginal areas of a measuring volume, U.S. Pat. No. 5,815,265 discloses the provision of specially shaped diaphragms in the illumination and stray light beam path. Apart from optomechanical elements, there are once again electronic components, particularly a light source and a light detector, which are constructionally connected to the measuring arrangement in a not further defined manner.

Thus, it is considered disadvantageous in the known methods and apparatuses that as a result of the constructional proximity, particularly the combination of measuring points and electronic components, a use in explosion-endangered environments is virtually excluded, at least without adopting additional costly measures. As a result of the known, compact constructional forms, measurement at difficultly accessible locations, e.g. on high chimneys or the like when measuring waste gases is not possible, if the in part sensitive and expensive electronic components are not to be exposed to damaging meteorological influences and must also be readily accessible. In known systems where a single light source is used for illuminating several measuring volumes, due to intensity losses on the optical components used for beam division, an illumination of different measuring volumes with an identical intensity is generally not ensured, which can have a negative effect during the evaluation of the measured results.

Even for the same design series, different particle counters have the disadvantage of different equipment characteristics. In the case of filter testing with a particle counter it is necessary to have a scanner, which is used upstream of the particle counter. In addition, there is a need for long sampling tubes from the sampling location to the scanner. An important disadvantage is the particle losses in the tubes.

With irregularly shaped particles such as e.g. with quartz dust or salt aerosols the stray light becomes higher due to a higher reflection percentage. Therefore an excessive diameter is measured. Finally the known sensors have a considerable weight.

The problem of the invention is to provide a method and an apparatus with which there is an intense illumination with high efficiency and in particular an identical irradiation of a plurality of measuring volumes and therefore there is an optimum comparability of the corresponding measured results.

SUMMARY OF THE INVENTION

According to the invention the set problem is solved with a method of the aforementioned type, in that the illumination of the measuring volume takes place by means of at least one radiation source positioned upstream of a concave mirror. In an apparatus constructed for performing the method, the at least one irradiating device has a radiation source and a concave mirror.

According to a preferred development of the method, at least two light beams are coupled out of an illuminating device having the concave mirror with recording optics inclined to the axis of symmetry of the concave mirror for the purpose of relaying.

According to preferred developments of the apparatus, the radiation source is constructed as a white light source, e.g. as a high pressure xenon lamp and that a concave mirror is constructed and/or the radiation source is arranged in such a way within the concave mirror that parallel to a focal plane of the concave mirror there is an annular surface traversed by a homogeneous radiant flux and in particular one or more optical waveguides with their recording optics are provided for coupling in radiation in the vicinity of the annular surface and are in particular inclined to the axis of symmetry of the concave mirror.

According to an extremely preferred development of the invention, a plurality of different fluid volumes are irradiated by means of an irradiating device through which a limited surface located outside the irradiating device is transilluminated with a radiation having a substantially homogeneous intensity throughout the surface. For this purpose the invention provides for the coupling of several light beams from an illuminating device having a concave mirror with recording optics inclined to the axis of symmetry of the concave mirror for relaying purposes.

The aforementioned, limited surface of homogeneous radiation intensity is inventively formed in that a concave mirror is so constructed and/or the radiation source is so arranged within the concave mirror, that parallel to a focal plane of the concave mirror there is an annular surface traversed by a homogeneous radiant flux. According to the invention, additionally one or more optical waveguides with their recording optics are provided for coupling in radiation in the vicinity of the annular surface and are in particular inclined to the axis of symmetry of the concave mirror. This ensures that in the case of several optical waveguides, into each waveguide can be coupled a substantially identical radiation intensity.

This offers the advantage that equipment characteristics such as resolving power, classification precision and count efficiency of the two or more sensor units are substantially identical. These equipment characteristics are dependent on the optoelectronic components both on the transmitting and receiving sides.

In order to permit precise measurements on particle flows embedded in fluids, particularly in explosion-endangered and/or damaging environments, as well as at difficultly accessible locations, e.g. on high chimneys or the like, the measurement is performed constructionally separated from at least one irradiating device and at least one receiver device in at least one sensor arrangement, through which flows a fluid flow containing the particles to be measured, that in the at least one sensor arrangement there is signal formation of a signal to be received in the receiver device using exclusively optomechanical elements and that signals are transmitted between the at least one sensor arrangement and the at least one irradiating device or the at least one receiver device by means of optical signal transmitters or that the at least one sensor arrangement is structurally separate from the irradiating device and the receiver device, that the at least one sensor arrangement is exclusively formed from optomechanical elements and that for a signal transmission between the at least one sensor arrangement and the at least one irradiating device or the at least one receiver device optical signal transmitters are provided.

As a result of the structural separation between optical and mechanical elements on the one hand and electronic components on the other, the method or apparatus according to the invention can also be used in explosion-endangered or damaging environments and in particular on difficultly accessible locations, because only the sensor arrangement exclusively having optomechanical elements has to be installed at the measurement location. All parts used which incorporate electronic components and which therefore are subject to strict safety requirements regarding use in explosion-endangered areas and which are also susceptible to external influences such as temperature and moisture, can be housed at a suitable location remote from the actual measurement point. Thus, the method and apparatus according to the invention have extended useability compared with the prior art. Thus, on the basis of a single central illuminating device and a similar detecting device, it is possible to operate a network of measurement points, which can be located at different critical locations of a particle or fluid flow, e.g. upstream and downstream of an exhaust gas flow filtering system.

According to a preferred development, signals are transmitted between the sensor device and the irradiating or receiver device by means of optical waveguides. This permits an efficient, inexpensive signal transmission, which can also take place in structurally difficultly accessible areas. In order to permit precise measurements, the invention provides for the at least one sensor arrangement to have at least one first imaging optics and at least one first diaphragm for irradiating at least one fluid volume, whose aperture has an edge convexly constructed towards the interior thereof and in which the edge is in particular T or H-shaped.

According to a further preferred development of the invention, the at least one sensor arrangement has at least one second imaging optics and at least one second diaphragm for observing part of the irradiated fluid volume and which in an extremely preferred development also has an aperture with convex edges. Thus, in the case of simultaneous use of a suitable evaluation electronics, a correction of the measured results obtained can take place in that the aberrational influence of particles in marginal areas of a measuring volume is reduced.

The observation of an irradiated fluid volume preferably takes place under a finite angle with respect to an irradiating device and in a further preferred development an observation angle of approximately 90° with respect to the irradiating device is chosen. Particularly in the case of particles in the micrometer range, an observation angle of 180° can be appropriate, because such particles preferably scatter light in the forward direction.

In order to be able to process and evaluate the signals of a plurality of sensor arrangements in quasi-simultaneous manner, according to a preferred development of the invention, the at least one receiver device is operated in a time multiplex. Preferably, for this purpose, upstream of a signal irradiation opening of the receiver device is positioned a beam interrupter. According to a development of the invention, the latter is constructed as a circular disk, rotatable about an axis perpendicular to its surface, with an opening spaced from a circle centre. Thus, at a specific time point, only the signal from a specific sensor arrangement enters the receiver device.

According to the invention a plurality of optical waveguides is positioned on a side of the beam interrupter remote from the receiver device in such a way that on rotating the beam interrupter per time unit only one radiation of a single optical waveguide can be beamed into the receiver device.

In order to also permit the measurement of the complete particle size and concentration of mixtures of solid particles and liquid droplets embedded in a fluid, according to a further development of the invention, a fluid flow is successively guided through at least two sensor arrangements, between which is in each case provided a heating device for heating the fluid flow. Preferably through the heating devices it is possible to reach fluid temperatures of up to approximately 400° C., so that e.g. oil droplets contained in an exhaust gas are evaporated, in order to limit the measurement to solid particles. According to the invention, one or more of the at least two sensor arrangements can be heated. Preferably in the sensor arrangements temperatures of up to 250° C. can be reached, so that volatile substances, which are possibly also adsorbed on the surfaces of solid particles, are eliminated.

Thus, the invention leads to the following advantages:

The use of small, replaceable sensors without electronics with measuring volumes of different sizes for measuring different maximum concentrations is possible in explosion-endangered environments. Two or more sensors have the same light source and the same detector. The equipment characteristics of this measuring system are consequently horizontal. The simultaneous stray light measurement of at least 2×90° or more on a single detector permits the precise diameter determination of irregularly shaped particles by means of optical averaging. Through the series connection of two sensors with different measuring volume sizes and alternating stray light detection, measurement can take place in a larger concentration range and/or particle size measuring range. At least two size ranges, such as 0.3 to 17 μm and 0.7 to 40 μm can consequently be measured at once.

BRIEF DESCRIPTION OF THE DRAWINGS

Further advantages and features of the invention can be gathered from the claims and the following description of embodiments with reference to the attached drawings, wherein show:

DETAILED DESCRIPTION RELATIVE TO THE DRAWINGS

Figure 1:
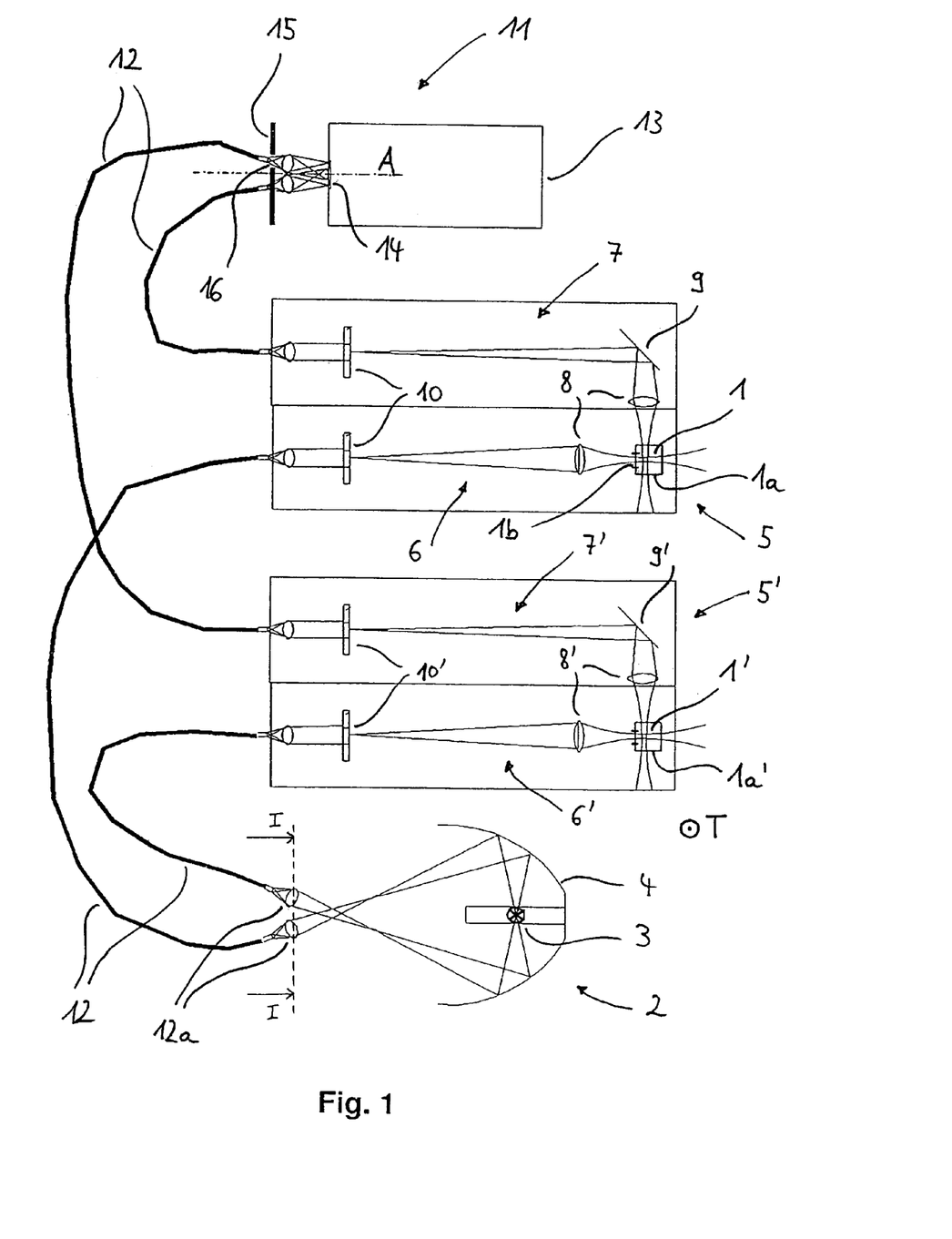
FIG. 1 A diagrammatic view of an apparatus according to the invention with an illuminating device, a receiver device and two sensor arrangements.

In the embodiment shown in FIG. 1 the apparatus according to the invention for the measurement of particle characteristics has two sensor arrangements 5, 5'. Each sensor arrangement 5, 5' has a line 1a, 1a' carrying a particle flow 1, 1' and whose wall has a transparent construction or a transparent window 1b (only window 1b in line 1a is shown in exemplified manner, but wherever light beams cross the wall of the line 1a, 1a' such a window 1b is provided). There is also an illuminating device 2 with a light source 3, preferably a white light source, upstream of a concave mirror 4 or within the contour thereof, from which illumination takes place of the particle flow 1 with a flow direction T perpendicular to the plane of the sheet, for measuring a particle flow in a fluid, e.g. an aerosol.

The sensor arrangements 5, 5' have in each case an irradiating optics 6, 6' and an imaging optics 7, 7', which exclusively have optomechanical components such as lenses 8, 8', mirrors 9, 9' and diaphragms 10, 10' (cf. FIGS. 7a, b), but no electrical or electronic elements. A receiver device 11 has a photodetector 13, e.g. a photomultiplier, with a signal irradiating opening 14 and a signal interrupter 15 positioned upstream thereof and which in the embodiment shown is constructed as a rotatable circular disk with an eccentrically positioned opening 16.

The transmission of light signals between the irradiating device 2, sensor arrangements 5, 5' and receiver device 11 takes place by means of optical waveguides 12, e.g. in the form of fibre glass cables. The signal supplied by the photodetector 13 is processed in a following, not shown electronics, which can be constructionally combined with the photodetector.

Figure 2:
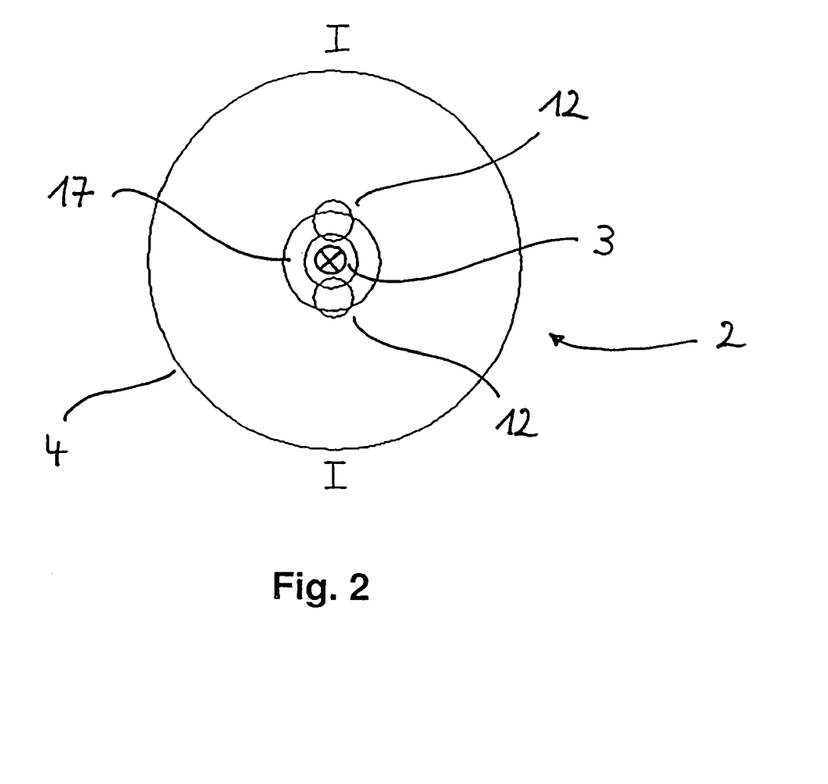
FIG. 2 A sectional view along line I—I of FIG. 1.

In the embodiment shown here the light source 3 is located slightly outside a focus of the concave mirror 4, so that the light beams do not leave the said mirror as parallel light bundles, but instead form a light circle 17 shown in FIG. 2.

Figure 3:
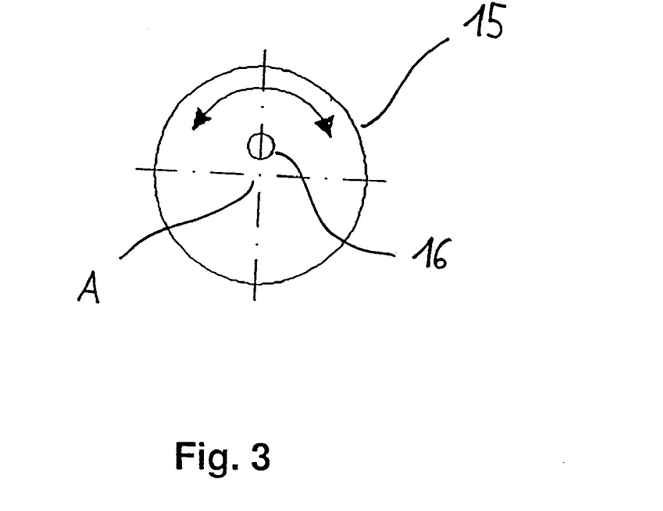
FIG. 3 A development of a beam interrupter according to the invention.

FIG. 2 shows the arrangement of the light source 3 within the concave mirror 4 of the illuminating device 2, as used in the embodiments of FIGS. 1 to 3. Through the arrangement of the light source 3 outside the focus of the concave mirror 4, upstream of the concave mirror 4 is formed an annular light circle 17, i.e. an annular surface, which is surface-traversed by a substantially homogeneous light flow. In the embodiment shown, there are two optical waveguides 12 in the vicinity of the light circle 17 and have at their ends recording optics 12a for coupling the light into the optical waveguides 12 and are positioned outside the axis of symmetry of the concave mirror and are oriented at different angles thereto, so that in each case the same light quantity is coupled into the optical waveguides 12.

Thus, the same light quantity is coupled into a plurality of optical waveguides 12 (FIG. 1). By means of the optical waveguides 12, in the embodiment shown, the coupled in light quantity is passed to the two sensor arrangements 5, 5', in which a certain partial volume of the particle flow 1, 1' is illuminated with the aid of the irradiating optics 6, 6'. If, according to the invention, T-diaphragms or H-diaphragms 10, 10' are used, as a result of the special geometry of the optical measuring volume and in the case of corresponding signal evaluation, a marginal zone error can be substantially avoided.

The particles contained in the fluid 1, 1' scatter the irradiated light. In the embodiment shown a stray light detection takes place under an angle of 90° and the stray light emitted by the particles under this angle is coupled with the aid of the imaging optics 7, 7' back into the optical waveguides 12, which ensure a relaying to the receiver device 11.

As a result of the flexible positioning of the sensor arrangements 5, 5' due to the use of optical waveguides 12, the invention permits a simultaneous measurement of particle sizes and concentrations in the case of a plurality of particle flows and/or at different points within a particle flow, e.g. for filter testing in a crude gas and a pure gas with a filter positioned between them. Thus, in the embodiment shown the photodetector 13 is operated in time multiplex. A time-separated irradiation of the sensor signals into the signal irradiation opening 14 of the photodetector 13 is brought about with the aid of a chopper-like, rotating beam interrupter 15, shown in greater detail in exemplified manner in FIG. 3.

FIG. 3 shows an embodiment of the beam splitter 15 according to the invention as a rotary circular disk, which has a circular opening 16 arranged in an eccentric manner. The circular disk 15 can be rotated about a rotation axis A, so that by means of the opening 16 in a time sequence corresponding to the disk rotation speed only the radiation of in each case one of the signal sources located on a circle can traverse the beam interrupter 15.

Figure 4:
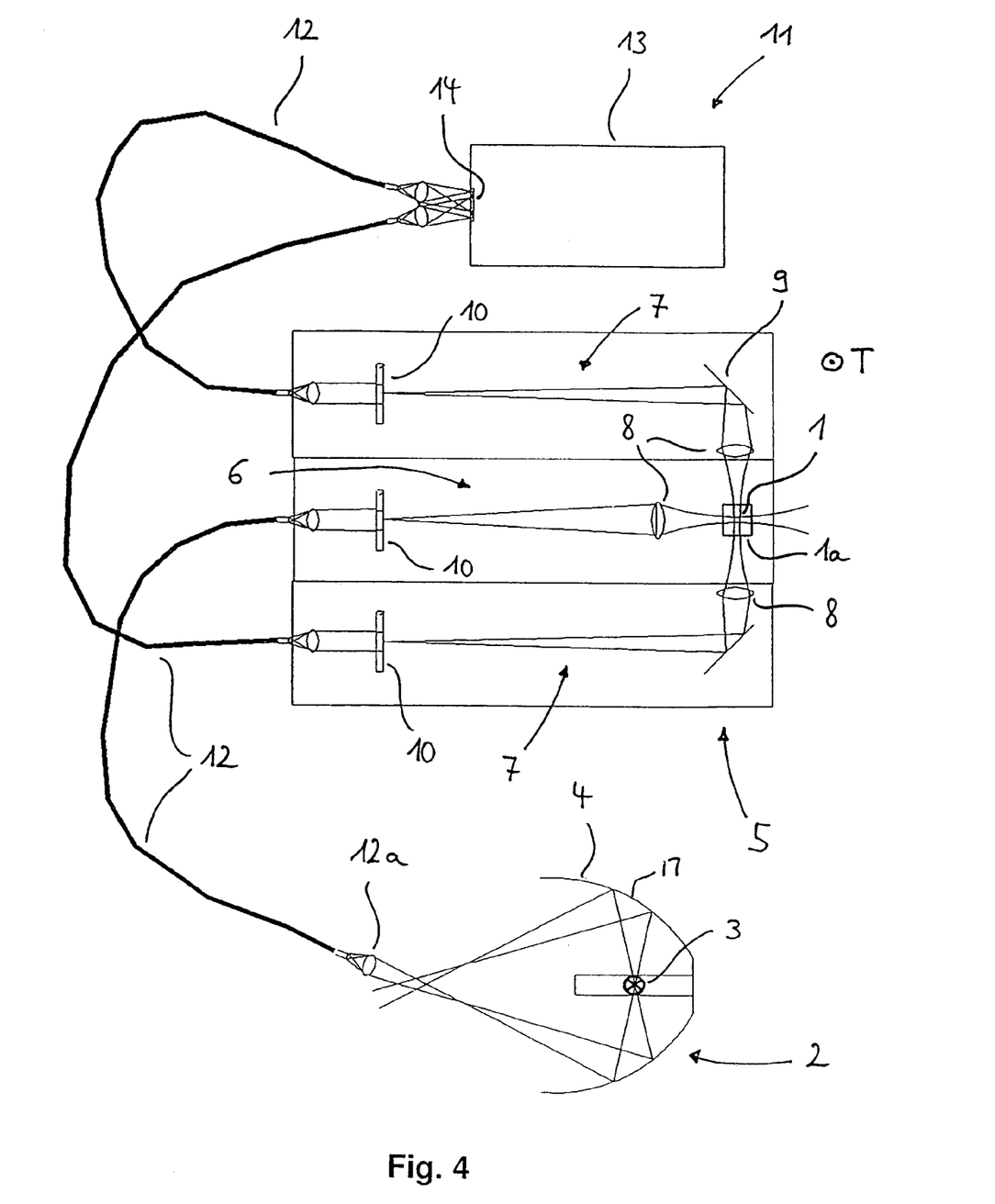
FIG. 4 A diagrammatic representation of an apparatus according to the invention with a single sensor arrangement.

FIG. 4 shows in another embodiment a development of the inventive apparatus essentially corresponding to that of FIG. 1. However, here in the case of an illuminated measuring volume of the particle flow 1, besides the irradiating optics 6 used for illumination purposes, there are two imaging optics 7 and 7' with which it is possible to detect the light scattered on the particles under two different angles, for example. 90 and 270°. The stray light is once again passed with optical wavegu ides 12 to a photodetector 13, where it is jointly irradiated into the signal irradiation opening 14 of said photodetector 13. Thus, also irregularly shaped particles, particularly with smooth surfaces can be reliably detected and which reveal a high degree of irregular, direction-selective scatter behaviour. It is also possible to separately evaluate the channels associated with the different stray angles in order to permit an evaluation of the measurements for comparison purposes.

Figure 5:
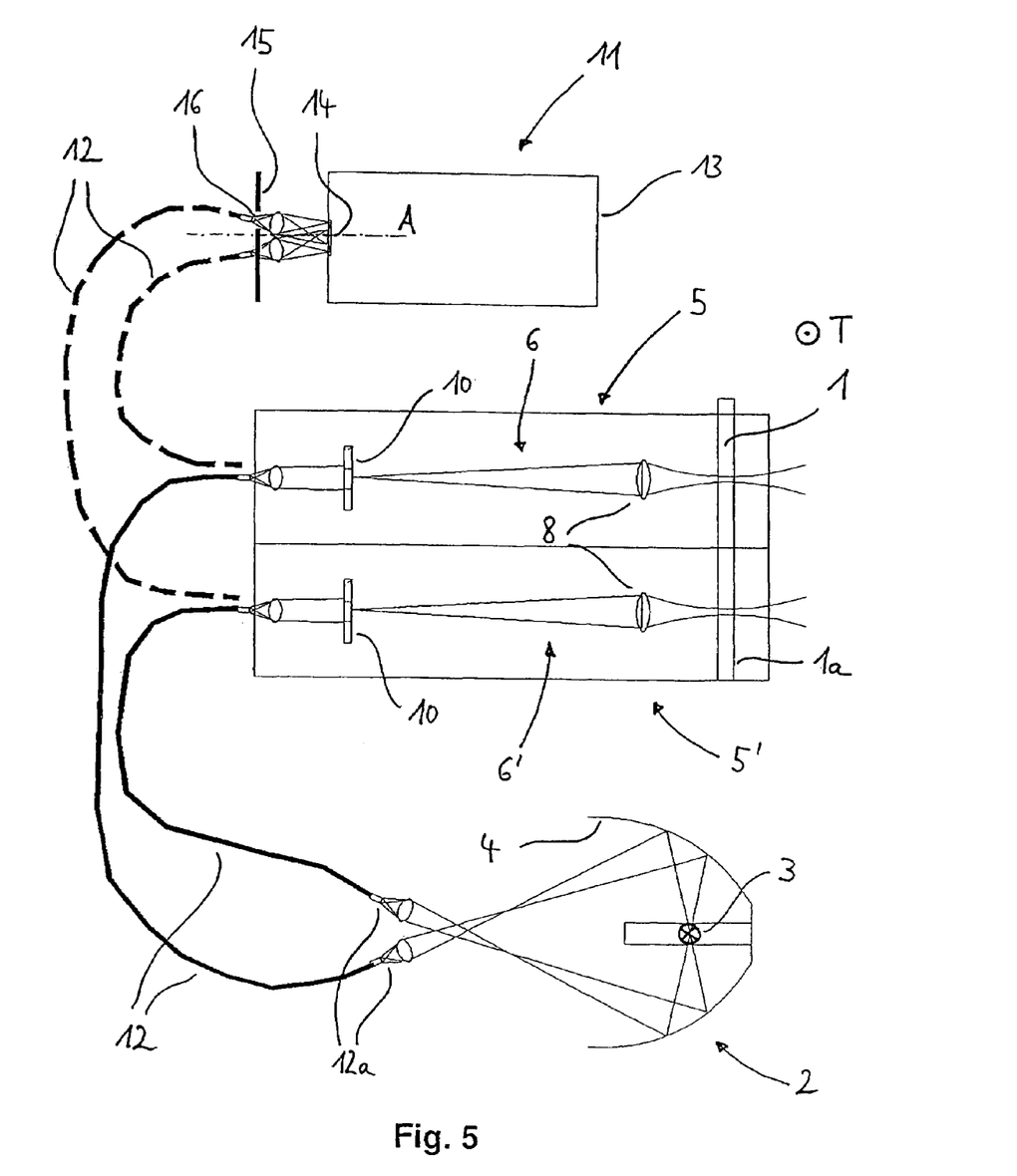
FIG. 5 A diagrammatic representation of a further apparatus according to the invention.

FIG. 5 shows another embodiment of an apparatus according to the invention in which a plurality of measuring volumes are connected in series within a particle flow 1. As in the embodiments of FIGS. 1 and 2, the sensor arrangements 5, 5' in each case have an irradiating optics 6, 6' and an imaging optics, which are not expressly shown here to make study of the drawing easier.

As a result of the series connection of several measuring volumes, in the case of the use of correspondingly different irradiating optics 6, 6' and imaging optics 7, 7', it is possible to bring about a joint detection of a corresponding plurality of particle size measuring ranges, e.g. 0.25 to 17 µm and 0.6 to 45 µm. The operation of the receiver device 11 takes place in the manner discussed relative to FIG. 1 in time multiplex using a beam interrupter 15.

Figure 6:
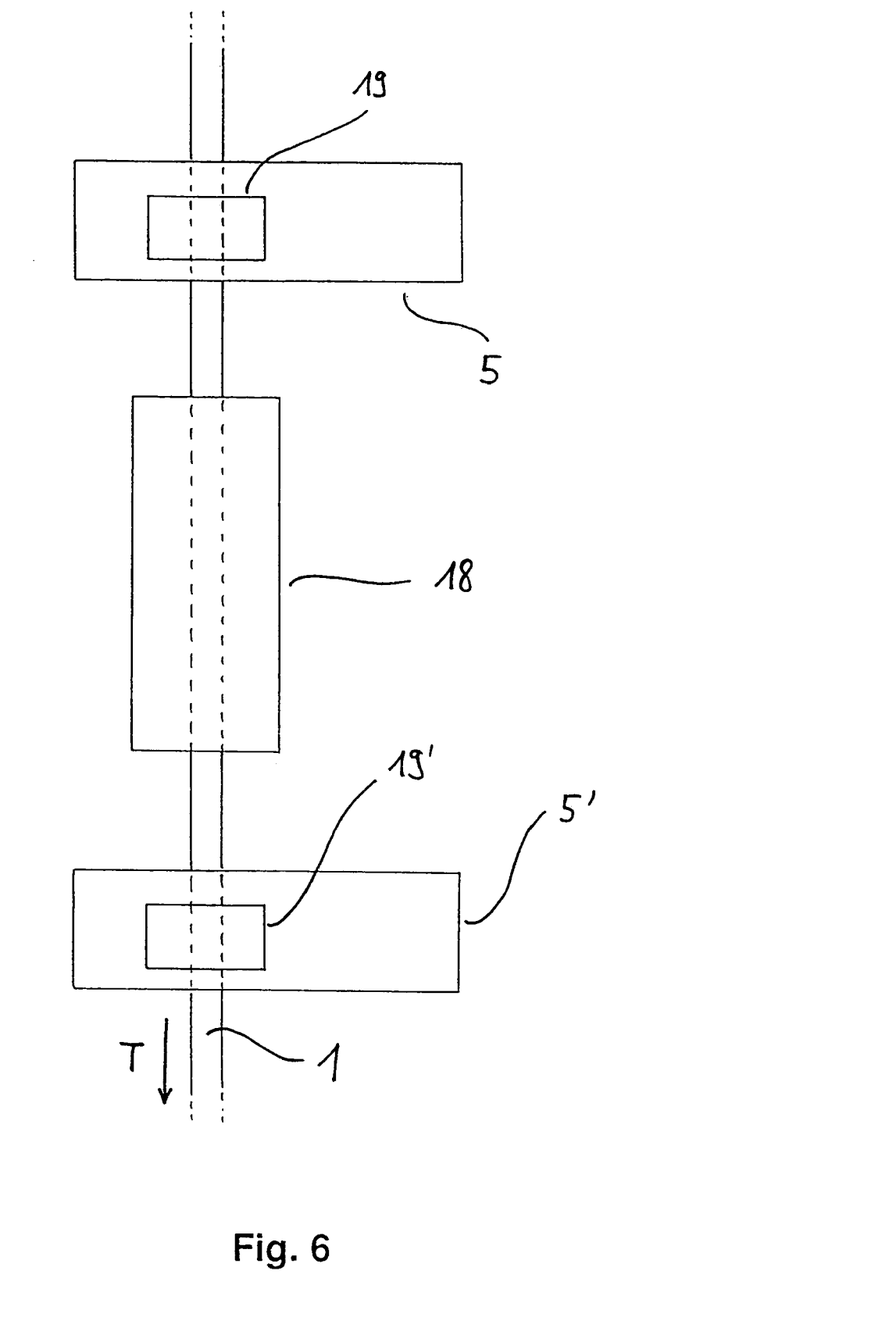
FIG. 6 Two sensor arrangements and a heating element according to the invention.

FIG. 6 shows a specific embodiment with two spatially separated sensor arrangements 5, 5' according to FIG. 1, which are traversed by the single identical particle flow 1. Between the sensor arrangements 5, 5' is provided a heating device 18, which is also traversed by the particle flow 1. The sensor arrangements 5, 5' incorporate heating devices 19, 19', which are located in areas of the sensor arrangements 5, 5' traversed by the particle flow 1.

With the aid of the heating devices contained in the sensor arrangements 5, 5', fluid temperatures up to 250° C. can be obtained. However, with the separate heating device 18 temperatures up to 400° C. can be obtained, so that any liquid droplets, e.g. oil droplets in the fluid are evaporated. In addition to a measurement of the total particle size and concentration in the sensor arrangement 5, the sensor arrangement 5' only provides information concerning the dust proportion in the fluid. With a suitable signal evaluation, separate informations are obtained in this way concerning the solid and liquid content of fluids, particularly aerosols.

Figure 7A:
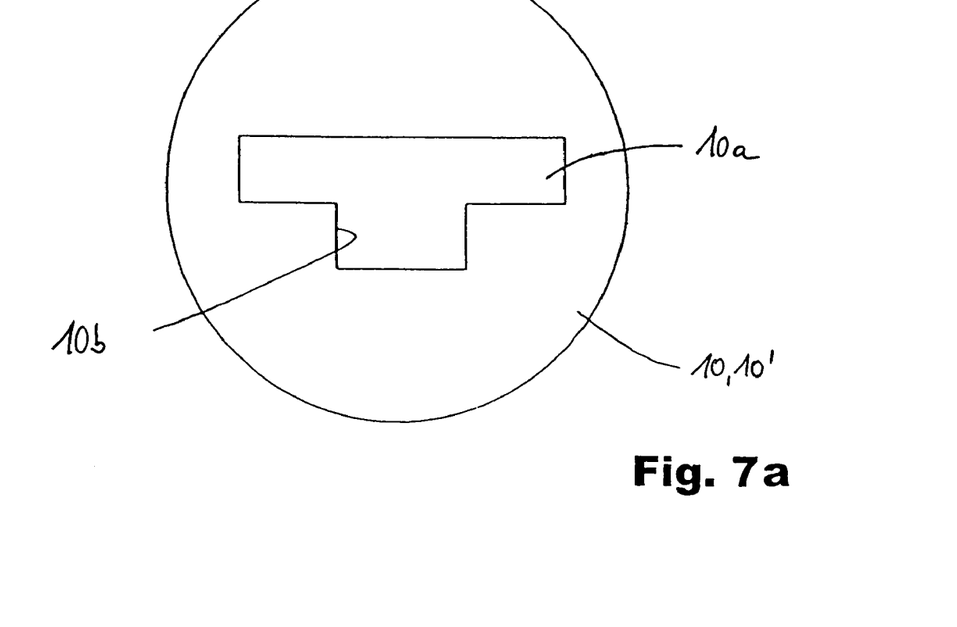
FIGS. 7a, b Developments of apertures according to the invention.
Figure 7B:
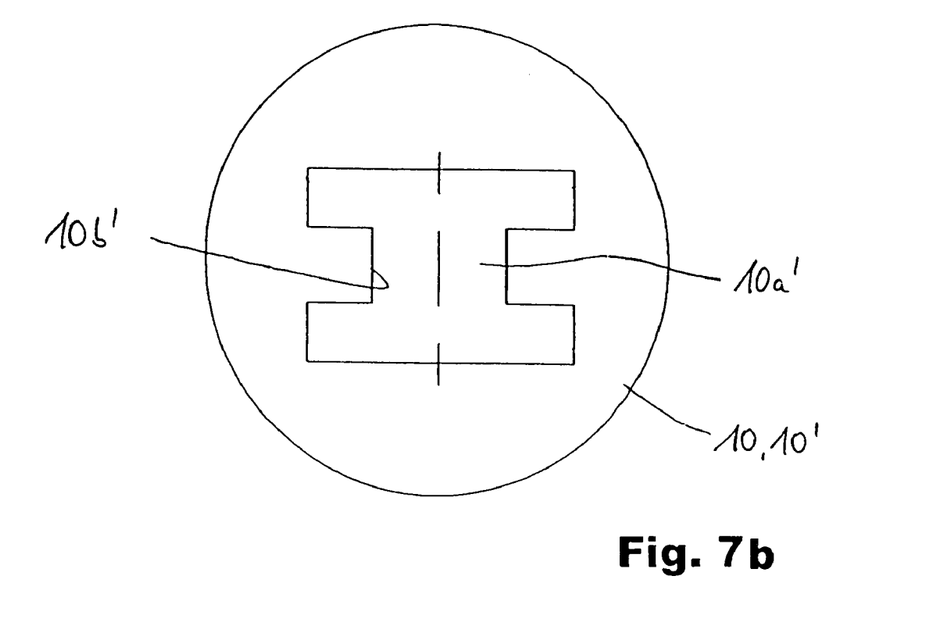

FIGS. 7a, b show preferred developments of the diaphragms 10, 10' according to the invention (FIGS. 1, 4 and 5). FIG. 7a shows a diaphragm 10 with a T-shaped aperture 10a, whose edge 10b is constructed in an inwardly convex manner. FIG. 7b shows a H-shaped aperture 10a', whose edge 10b' is also constructed in convex manner towards the aperture interior and as a result measurement can take place in marginal zone error-free manner.

The invention claimed is:

1. A method for measuring characteristics of particles in a fluid by detecting electromagnetic radiation scattered on individual particles in at least one measuring volume, wherein illumination of the measuring volume takes place by means of at least one radiation source positioned upstream of a concave mirror and at least two light beams from an illuminating device having the concave mirror are coupled out to the at least one measuring volume with optics including optical waveguides having respective recording optics inclined to an axis of symmetry of the concave mirror and coupling light into the optical waveguides.

2. A method according to claim 1, including measuring different size measuring volumes in at least one fluid flow.

3. A method according to claim 1, wherein for each radiation source one measuring volume is simultaneously observed from directions in space.

4. A method for measuring characteristics of particles in a fluid by detecting electromagnetic radiation scattered on individual particles in at least one measuring volume, wherein illumination of the measuring volume takes place by means of at least one radiation source positioned upstream of a concave mirror and at least two light beams from an illuminating device having the concave mirror are coupled out of the concave mirror to the at least one measuring volume with optics inclined to an axis of symmetry of the concave mirror, wherein in at least one sensor arrangement a fluid-through-flowed measuring volume is illuminated using at least one first diaphragm, whose aperture has an edge constructed convexly towards an interior of the aperture.

5. A method according to claim 4, wherein the measuring volume is observed using at least one second diaphragm, whose aperture has an edge constructed convexly towards an interior of the aperture.

6. A method according to claim 4, wherein signals are transmitted between a sensor arrangement and an irradiating device or a receiver device by means of optical waveguides.

7. A method for measuring characteristics of particles in a fluid by detecting electromagnetic radiation scattered on individual particles in at least one measuring volume, wherein illumination of the measuring volume takes place by means of at least one radiation source positioned upstream of a concave mirror and at least two light beams from an illuminating device having the concave mirror are coupled out of the concave mirror to the at least one measuring volume with optics inclined to an axis of symmetry of the concave mirror, wherein a plurality of different fluid volumes are illuminated with substantially identical intensity, by means of an irradiating device through which a surface located outside an irradiating device is illuminated with radiation having a substantially homogeneous intensity throughout the surface.

8. A method for measuring characteristics of particles in a fluid by detecting electromagnetic radiation scattered on individual particles in at least one measuring volume, wherein illumination of the measuring volume takes place by means of at least one radiation source positioned upstream of a concave mirror and at least two light beams from an illuminating device having the concave mirror are coupled out of the concave mirror to the at least one measuring volume with optics inclined to an axis of symmetry of the concave mirror 4, wherein a fluid flow after flowing through a first sensor arrangement and before flowing through a second sensor arrangement is heated for evaporation of at least one component contained in the fluid flow.

9. A method for measuring characteristics of particles in a fluid by detecting electromagnetic radiation scattered on individual particles in at least one measuring volume, wherein illumination of the measuring volume takes place by means of at least one radiation source positioned upstream of a concave mirror and at least two light beams from an illuminating device having the concave mirror are coupled out of the concave mirror to the at least one measuring volume with optics inclined to an axis of symmetry of the concave mirror, and including using a larger number of sensor arrangements than the number of receiver devices, and operating the sensor arrangements in a time multiplexed manner.

10. A method according to claim 9, wherein sensor signals entering a receiver device are input in a time-separated manner into said receiver device by a beam interrupter.

11. A method for measuring characteristics of particles in a fluid by detecting electromagnetic radiation scattered on individual particles in at least one measuring volume, wherein illumination of the measuring volume takes place by means of at least one radiation source positioned upstream of a concave mirror and at least two light beams from an illuminating device having the concave mirror are coupled out of the concave mirror to the at least one measuring volume with optics inclined to an axis of symmetry of the concave mirror, wherein the measurement of characteristics takes place structurally separated from at least one irradiating device and at least one receiver device in at least one sensor arrangement through which flows a fluid flow containing the particles to be measured, that in the at least one sensor arrangement signal formation of a signal to be received in the at least one receiver device takes place using exclusively optomechanical elements and that signals are transmitted between the at least one sensor arrangement and the at least one irradiating device or the at least one receiver device by means of optical signal transmitters.

12. An apparatus for measuring characteristics of particles in a fluid by detection of electromagnetic radiation scattered on individual particles in at least one measuring volume, said apparatus comprising at least one illuminating device, at least one receiver device, at least one sensor arrangement through which flows a fluid flow containing the particles to be measured, and wherein the at least one illuminating device has a radiation source and a concave mirror said radiation source being positioned upstream of the concave mirror, and optics including optical waveguides having respective recording optics inclined to an axis of symmetry of the concave mirror for coupling light into the optical waveguides to couple light beams from the at lest one illuminating device to the at least one measuring volume.

13. An apparatus according to claim 12, wherein the radiation source is constructed as a white light source.

14. An apparatus according to claim 12, wherein a concave mirror is constructed and/or the radiation source is arranged in such a way within the concave mirror, that parallel to a focal plane of the concave mirror there is an annular surface traversed by a homogeneous radiant flux.

15. An apparatus according to claim 12, wherein the at least one sensor arrangement has at least one first imaging optics with at least one first diaphragm for irradiating at least one fluid volume and whose aperture is constructed with convex edges, comprising a T or H-shape.

16. An apparatus according to claim 12, wherein the optical waveguides provide essentially identical electromagnetic radiation intensity from the radiation source and the concave mirror to the at least one measuring volume.

17. An apparatus according to claim 15, wherein the at least one sensor arrangement has at least one second imaging optics with at least one second diaphragm for observing at least part of the irradiated fluid volume.

18. An apparatus according to claim 17, wherein the aperture of the second diaphragm is constructed with convex edges, comprising a T-or H-shape.

19. An apparatus according to claim 18, wherein at least one second diaphragm and the at least one second imaging optics for observing the irradiated fluid volume are arranged with a finite angle with respect to an illuminating device.

20. An apparatus according to claim 19, wherein the angle is approximately 90°.

21. An apparatus according to claim 12, wherein the at least one receiver device is operable in a time multiplexed manner.

22. An apparatus according to claim 21, wherein a beam interrupter is positioned upstream of a signal irradiation opening of the at least one receiver device.

23. An apparatus according to claim 22, wherein the beam interrupter is constructed as a circular disk rotatable about an axis perpendicular to the surface thereof and having an opening spaced from a center of the circle.

24. An apparatus according to claim 23, wherein the optical waveguides are positioned on a side of the beam interrupter remote from the at least one receiver device so that on rotating the beam interrupter at any one time only one beam of a single waveguide can be irradiated into the at least one receiver device.

25. An apparatus for measuring characteristics for measuring characteristics of particles in a fluid by detection of electromagnetic radiation scattered on individual particles in at least one measuring volume, said apparatus comprising at least one illuminating device, at least one receiver device, at least one sensor arrangement through which flows a fluid flow containing the particles to be measured, wherein the at least one illuminating device has a radiation source and a concave mirror, said radiation source being positioned upstream of the concave mirror, and optics including optical waveguides in the form of respective fiber glass cables having respective recording optics inclined to an axis of symmetry of the concave mirror for coupling light into the optical waveguides to couple light beams from the at least one illuminating device to the at least one measuring, and wherein a fluid flow is successively guided through at least two sensor arrangements, between which for each arrangement is provided a heating device for heating the fluid flow.

26. An apparatus according to claim 25, wherein the heating device provides fluid temperatures up to approximately 400°.

27. An Apparatus according to claim 26, wherein one or more of the at least two sensor arrangements can be heated.

28. An apparatus according to claim 27, wherein temperatures of approximately 250° C. can be reached in the sensor arrangements.

29. An apparatus for measuring characteristics of particles in a fluid by detection of electromagnetic radiation scattered on individual particles in at least one measuring volume, said apparatus comprising at least one illuminating device, at least one receiver device, at least one sensor arrangement through which flows a fluid flow containing the particles to be measured, wherein the at least one sensor arrangement is structurally separated from the illuminating device and the receiver device, the at least one sensor arrangement is constructed exclusively from optomechanical elements and for signal transmission between the at least one sensor arrangement and the at least one illuminating device or the at least one receiver device, optical signal transmitters are provided and wherein the at least one illuminating device has a radiation source and a concave mirror, said radiation source being positioned upstream of the concave mirror, and optics including optical waveguides having respective recording optics inclined to an axis of symmetry of the concave mirror for coupling light into the optical waveguides to couple light beams from the at least one illuminating device to the at least one measuring volume.

30. An apparatus according to claim 29, wherein the at least one illuminating device has a radiation source and a concave mirror.

31. An apparatus according to claim 29, wherein the signal transmitters are constructed as optical waveguides.

* * * * *